(12) United States Patent
Wollert et al.

(10) Patent No.: US 6,680,777 B1
(45) Date of Patent: Jan. 20, 2004

(54) AUTOMATIC TRANSMISSION FLUID TESTER

(75) Inventors: Gary S. Wollert, Kenosha, WI (US); Thomas P. Becker, Kenosha, WI (US)

(73) Assignee: Snap-On Technologies, Inc., Lincolnshire, IL (US)

( * ) Notice: Subject to any disclaimer, the term of this patent is extended or adjusted under 35 U.S.C. 154(b) by 204 days.

(21) Appl. No.: 09/709,462

(22) Filed: Nov. 13, 2000

(51) Int. Cl.[7] ................................. G01N 21/00
(52) U.S. Cl. .................. 356/436; 356/70; 123/196 S; 250/573
(58) Field of Search ................. 356/432–440, 356/70; 73/53.05, 293; 250/573, 577, 563, 574; 340/457.4, 450.3, 438; 475/65, 115; 123/196 S

(56) References Cited

U.S. PATENT DOCUMENTS

| | | | |
|---|---|---|---|
| 3,141,094 A | | 7/1964 | Strickler |
| 3,734,629 A | | 5/1973 | Griffiths et al. |
| 3,794,428 A | | 2/1974 | Giesecke |
| 3,811,837 A | * | 5/1974 | Hoffman ............... 436/40 |
| 3,892,485 A | * | 7/1975 | Merritt et al. |
| 4,003,661 A | | 1/1977 | Yamano |
| 4,035,086 A | | 7/1977 | Schoeffel et al. |
| 4,135,100 A | | 1/1979 | Harada et al. |
| 4,198,207 A | * | 4/1980 | Ladov et al. .......... 436/40 |
| 4,264,560 A | | 4/1981 | Natelson |
| 4,306,525 A | * | 12/1981 | Faxvog |
| 4,560,269 A | | 12/1985 | Baldszun et al. |
| 4,647,371 A | * | 3/1987 | Schmitt et al. ........ 210/96.1 |
| 4,677,567 A | * | 6/1987 | Grosser et al. ........ 700/268 |
| 4,687,327 A | * | 8/1987 | Wheeless ............... 356/70 |
| 4,699,509 A | | 10/1987 | Kamiya et al. |
| 4,867,559 A | | 9/1989 | Bach |
| 5,194,910 A | | 3/1993 | Kirkpatrick, Jr. et al. |
| 5,196,898 A | | 3/1993 | Tamura et al. |
| 5,438,420 A | | 8/1995 | Harwick et al. |
| 5,548,393 A | | 8/1996 | Nozawa et al. |
| 5,777,211 A | | 7/1998 | Binienda et al. |
| 5,828,458 A | | 10/1998 | Tylor et al. |

\* cited by examiner

*Primary Examiner*—Hoa Q. Pham
(74) *Attorney, Agent, or Firm*—McDermott, Will & Emery

(57) ABSTRACT

An automatic transmission fluid tester determines the remaining service life of automatic transmission fluid. The tester includes a radiation source for emitting radiation in the direction of an automatic transmission fluid sample under test, and a radiation receiver for detecting radiation passed through the sample. Based on the output of the radiation receiver, the tester measures the opacity of the sample. The remaining service life of the automatic transmission fluid is determined as a function of the measured opacity.

19 Claims, 5 Drawing Sheets

AUTOMATIC TRANSMISSION FLUID TESTER

FIELD OF THE INVENTION

The present invention relates to maintenance of automatic transmissions, and more specifically, to determining the remaining service life of automatic transmission fluid.

BACKGROUND ART

According to the Automatic Transmission Rebuilders Association of Ventura, Calif., over 11 million automatic transmission failures per year (nearly nine out of ten automatic transmission failures) are caused by degradation of automatic transmission fluid due to heat. Heat causes transmission fluid to change its chemical composition, and that compromises its performance and accelerates wear on internal components of automatic transmissions. To prevent such failures, the automatic transmission fluid must be changed before it reaches the end of its service life. This is typically done at periodic intervals, usually based on mileage. For example, the owner manuals of automobiles may recommend changing the automatic transmission fluid every 30,000 miles.

However, a number of factors, such as transmission temperature, ambient temperature, coolant temperature, number of shifts, and the like, actually determine the service life of automatic transmission fluid. Therefore, the service life of automatic transmission fluid can vary from car to car depending on how the car has been driven, and the climate and geographic conditions in which it has been driven. For example, the automatic transmission fluid in a car driven mainly on the freeway at a steady speed in a temperate climate will have a longer service life than the automatic transmission fluid in a car driven under severe driving conditions. In the former case, the automatic transmission fluid may well have a significant amount of its service life left at the end of the periodic mileage interval, whereas in the latter case, its service life may have been exceeded.

The remaining service life of transmission fluid is generally evaluated by an automotive technician based on the smell of the fluid and its visual inspection. An overheated transmission will burn the fluid resulting in a recognizable odor. However, it is hard to accurately determine the remaining service life of automatic transmission fluid based on its appearance and smell.

Accordingly, it would be desirable to create a device for determining the remaining service life of automatic transmission fluid.

SUMMARY OF THE INVENTION

The present invention offers a novel method of determining the remaining service life of automatic transmission fluid (ATF). The method involves emitting radiation in the direction of an ATF sample under test. The opacity of the ATF sample is measured based on the radiation passed through the ATF sample. The remaining service life of the ATF is determined as a function of the measured opacity.

Preferably, a signal indicative of the opacity may be compared with multiple calibration levels to determine the remaining service life of the ATF under test. Each of the multiple calibration levels may be established based on the intensity of radiation passed through the ATF having known length of life.

For example, the ATF sample may be irradiated with infrared radiation to provide consistent indication of the remaining service life for ATF of various types. Alternatively, the ATF sample may be irradiated with red light to increase the accuracy of determining the remaining service life of ATF as a function of the measured opacity.

In accordance with one aspect of the present invention, a system for testing ATF comprises a radiation source for emitting radiation in the direction of the ATF sample under test, a radiation receiver responsive to the radiation for producing an output signal representing the intensity of radiation passed through the ATF sample, and an output circuit responsive to the output signal for measuring the opacity of the ATF.

In an embodiment of the present invention, the output circuit is configured to compare the output signal with multiple calibration levels to provide a multiple level indication of the remaining service life of the ATF. Each of the calibration levels corresponds to the output signal of the radiation receiver produced in response to the radiation passed through the ATF having known length of life.

For example, each of the calibration levels may be maintained at the same level for testing ATF of any type. In this case, a source of infrared radiation is a preferable radiation source, because it provides more consistent indication of the remaining service life for various types of ATF.

Alternatively, the calibration levels may be set for testing ATF of a particular type. In this case, a source of red light is a preferable radiation source because it increases the accuracy of determining the remaining service life of ATF.

The ATF sample under test may be contained in a disposable container to prevent contamination of the testing system by previously tested ATF. A narrow slot may be provided between the radiation source and the radiation receiver for receiving the disposable container.

A radiation controller may be provided for controlling radiation emitted by the radiation source. The radiation controller may control the radiation source to make the intensity of the emitted radiation sufficient to traverse the ATF sample under test. For example, the radiation controller may control the radiation source so as to emit a predetermined sequence of radiation signals with progressively increasing intensity.

Still other aspects of the present invention will become readily apparent to those skilled in this art from the following detailed description, wherein an embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION OF THE INVENTION

In accordance with the present invention, the remaining service life of automatic transmission fluid is determined by measuring its opacity. Based on performed experiments, it was found that the opacity of transmission fluid is closely correlated with its remaining service life. The color of the fluid gets darker with age as it carries normal wear contaminants with it. For example, the color of automatic transmission fluid may change during service from a near transparent red to a dark semi-opaque brown.

Figure 1:
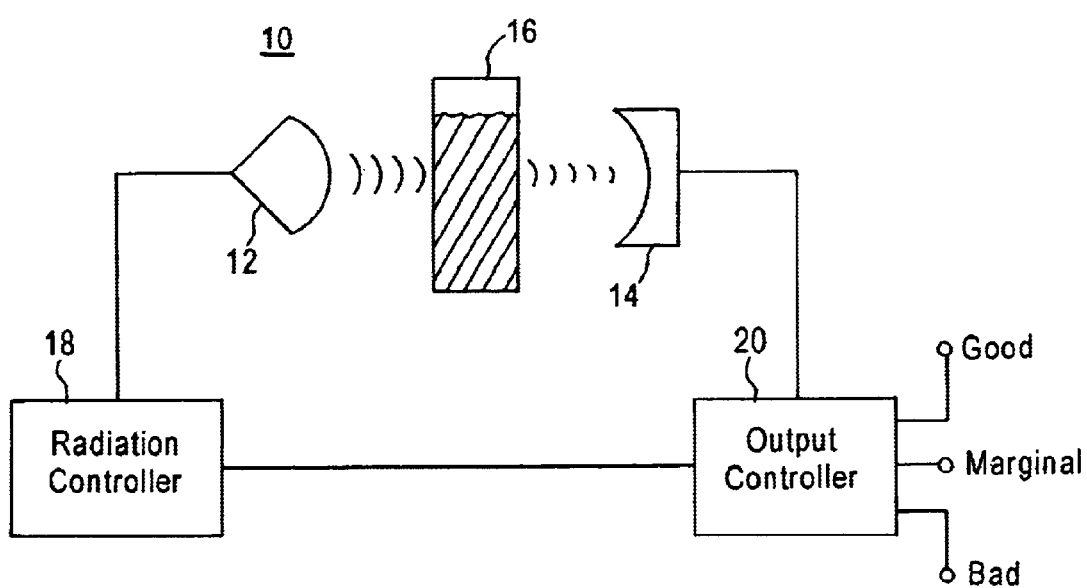
FIG. 1 is a block diagram of an automatic transmission fluid tester of the present invention.

Referring to FIG. 1, a transmission fluid tester 10 in accordance with an embodiment of the present invention comprises a radiation source 12, a radiation receiver 14, a sample section 16, a radiation controller 18, and an output controller 20. A sample of automatic transmission fluid under test is placed in the sample section 16 between the radiation source 12 and the radiation receiver 14. The signal emitted by the radiation source 12 is directed through the fluid sample to the radiation receiver 14 that supplies the output controller 20 with an output signal indicating the intensity of the light passing through the tested sample of transmission fluid. The output signal of the radiation receiver 14 corresponds to the intensity of the radiation passed through the fluid sample under test. Therefore, this output signal represents the opacity of the fluid sample.

Based on a calibration procedure described in more detail below, the output controller 20 analyzes the output signal of the receiver 14 to determine the condition of the fluid sample and make a decision as to the remaining service life of the automatic transmission fluid being tested.

In accord with an embodiment of the invention, an infrared radiation source such as an infrared light-emitting diode (LED) is used as the radiation source 12. It was found that the infrared radiation source provides the most consistent indication of transmission fluid serviceability for different types of automatic transmission fluid. However, the present invention may be implemented using various sources of radiation, such as an incandescent lamp or a red high-intensity LED.

Figure 2A:
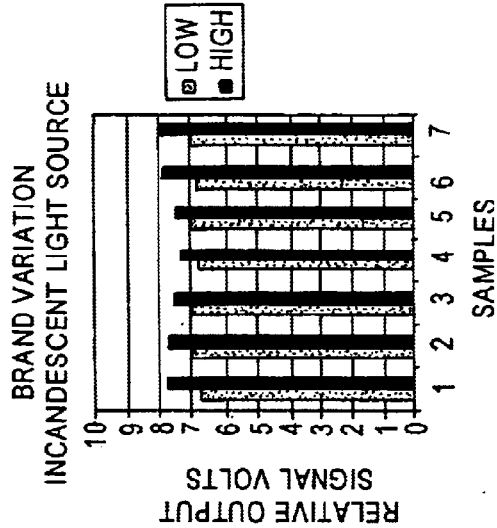
FIGS. 2A, 2B and 2C are diagrams illustrating variations of fluid remaining service life indication for the automatic transmission fluid tester using infrared, red and incandescent radiation sources, respectively, for different types of tested automatic transmission fluid.
Figure 2B:
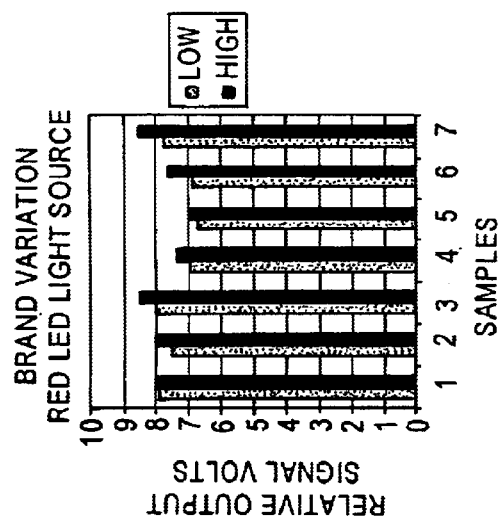
Figure 2C:
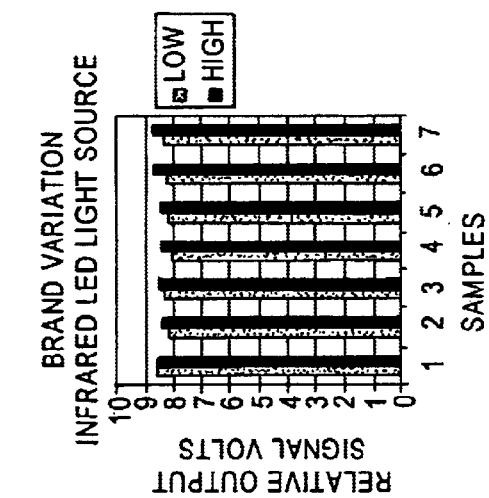

FIGS. 2A, 2B and 2C illustrate variations of fluid remaining service life indication for a transmission fluid tester using infrared, red and incandescent radiation sources, respectively, for different types of tested transmission fluid. As determined experimentally, the transmission fluid tester using an infrared LED has a 4.8% variation of serviceability indication for different brands of transmission fluid, whereas the transmission fluid tester using an incandescent lamp has a 5.76% variation, and the tester using a red high-intensity LED has a 19.53% variation. Bars "LOW" and "HIGH" respectively reflect low and high values of results obtained for each of seven different transmission fluid brands.

The radiation controller 18 controls a signal emitted by the radiation source 12 to make the intensity of this signal sufficient to pass through the fluid sample and trigger the radiation receiver 14. For example, the radiation controller 18 may control the radiation source 12 so as to emit a predetermined sequence of infrared signals with progressively increasing intensity.

The intensity of the emitted signal may be controlled by adjusting a value of voltage supplied to the radiation source 12. Also, a value of current supplied to the radiation source 12 may be controlled.

The output controller 20 is calibrated with multiple experimentally determined calibration values corresponding to different conditions of the transmission fluid sample under test. The calibration values are obtained based on radiation passed through samples of transmission fluid having known length of service life. The output controller 20 compares the output signal of the radiation receiver 14 to the calibration values to determine the remaining service life of the tested transmission fluid.

For example, the transmission fluid tester 10 may be calibrated to indicate the following three conditions of transmission fluid: good, marginal and bad. These conditions indicate the remaining service life of the tested automatic transmission fluid.

In particular, the good condition may be defined to correspond to practically new transmission fluid. The marginal condition corresponds to used transmission fluid, which does not reach the end of its service life. For example, the marginal condition may correspond to transmission fluid after 25,000 mile under normal driving conditions. As the service life under normal driving conditions may be about 30,000 miles, transmission fluid in the marginal condition still has a certain amount of the remaining service life.

The bad condition requires the tested transmission fluid to be changed. The bad condition may be defined for a specific amount of a service life under specific driving conditions. Respective visual or sound indicators may be arranged at the output of the output controller 20 to indicate good, marginal and bad conditions.

Figure 3A:
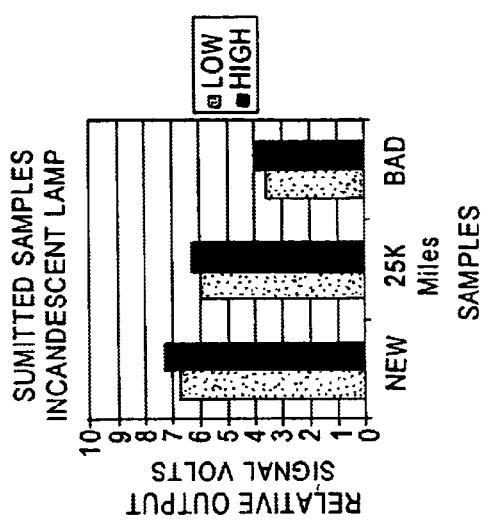
FIGS. 3A, 3B and 3C are diagrams illustrating exemplary calibration levels for the automatic transmission fluid tester using an infrared LED, a red high-intensity LED, and an incandescent lamp, respectively.
Figure 3B:
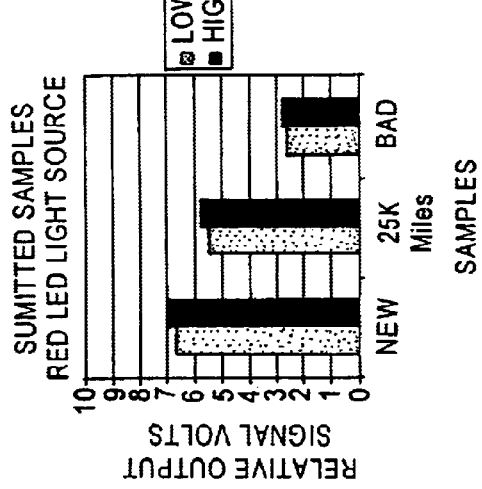
Figure 3C:
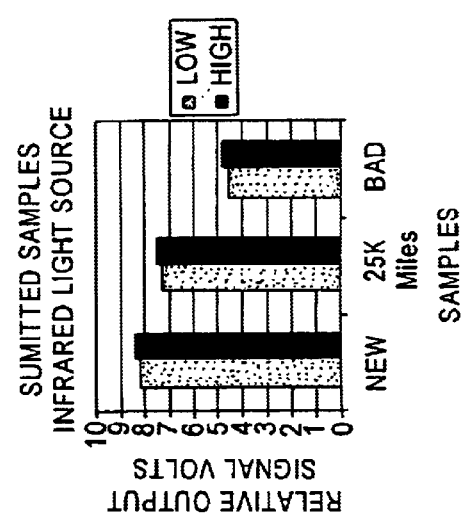

FIGS. 3A, 3B and 3C illustrate exemplary calibration levels for transmission fluid tester using an infrared LED, a red high-intensity LED, and an incandescent lamp, respectively. Bars "LOW" and "HIGH" respectively reflect low and high values of test results obtained for known transmission fluid samples, which are in good, marginal and bad conditions. For example, for the infrared LED, variation between calibration values for the good and bad conditions may be about 40%. For the red high-intensity LED, variation between calibration values for the good and bad conditions may be about 50%.

Depending on desired measurement accuracy, the transmission fluid tester of the present invention may be implemented using any number of calibration levels corresponding to known conditions of transmission fluid between the good condition and the bad condition. To increase measurement accuracy, a calibration procedure may be performed for each particular type of transmission fluid to be tested. In this case, for each type of transmission fluid, multiple calibration levels may be established to reflect different conditions of the particular transmission fluid type. As described above, a red-light source of radiation provides the largest variation between calibration levels for a good condition and a bad condition for a particular type of transmission fluid. Therefore, the accuracy of the remaining service life determination using a red LED is higher than for other sources of radiation.

The output controller 20 compares the output signal of the radiation receiver 18 with pre-set calibration levels to accurately determine the remaining service life of the transmission fluid under test The output signal and calibration levels may be represented by respective voltage or current values.

Figure 4A:
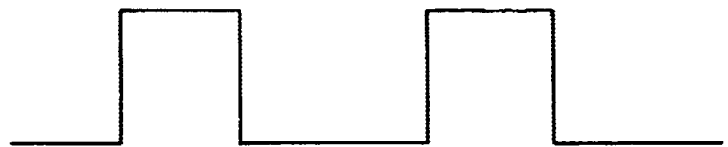
FIGS. 4A, 4A and 4C illustrate duty cycle values representing an automatic transmission fluid sample in good, marginal and bad conditions, respectively.
Figure 4B:
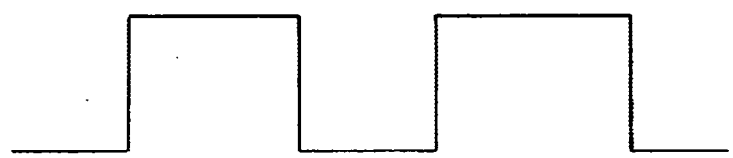
Figure 4C:
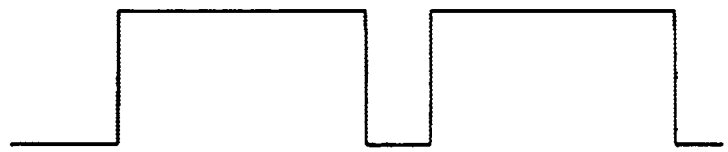

Alternatively, the radiation controller 18 may control the radiation source 12 to produce pulse radiation signals. Duty cycle values of pulse signals at the output of the radiation receiver 14 may be used as calibration values representing different conditions of transmission fluid. The duty cycle value of the signal at the output of the radiation receiver may be compared with the calibration duty cycle values to determine the condition of the transmission fluid under test. For example, greater. ON periods in an output signal cycle may correspond to worse transmission fluid conditions. FIGS. 4A, 4B and 4C illustrating exemplary output signal cycles representing good, marginal and bad conditions, respectively. The ON period of the pulse signal representing new automatic transmission fluid (FIG. 4A) is smaller that the ON period of the pulse signal representing automatic transmission fluid after 25,000 miles (FIG. 4B), which in turn is smaller than the ON period of the pulse signal representing automatic transmission fluid in a bad condition (FIG. 4C).

Figure 5:
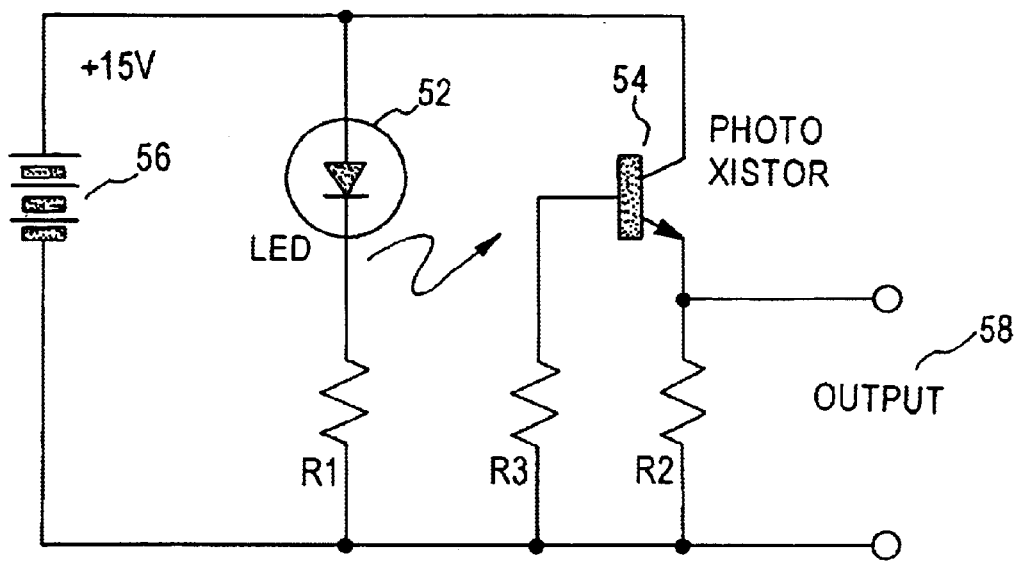
FIG. 5 is a simplified schematic circuit diagram of an exemplary automatic transmission fluid tester of the present invention.

FIG. 5 illustrates a simplified schematic circuit diagram of an exemplary transmission fluid tester of the present invention. The fluid tester 10 may comprise an infrared LED 52 that emits infrared radiation directed to an NPN phototransistor 54 arranged for detecting the infrared radiation passing through a transmission fluid sample. For example, a QT Optoelectronics Model F5E2 may be used as the LED 52, and a QT Optoelectronics Model LT14N2 may be used as the phototransistor 54.

A 15V DC power supply source 56 is used for both the infrared radiation generation and detection. An output controller may be connected to an output 58 of the phototransistor circuitry for monitoring the level of the infrared radiation passed through the transmission fluid sample, to determine the remaining service life of the transmission fluid in the sample. For example, the output controller may comprise a voltmeter connected across the output 58 to measure voltage at this output.

Resistor R1 limiting radiation source current is connected between the power supply source 56 and the LED 52. The resistor R1 may be adjusted to provide specified current through the radiation source 52.

Resistor R2 providing an emitter output load for the NPN transistor 54 is connected in parallel to the output monitored by the volt meter to enable the calibration of the volt meter. For example, the resistance value of the resistor R2 may be adjusted so as to provide a voltmeter reading of about one half of the supply voltage when new transmission fluid is tested.

Resistor R3 may be provided to shunt the input of the NPN phototransistor 54 to adjust its sensitivity. In particular, the resistor R3 shunts the phototransistor base when the output saturates due to excessive intensity of the infrared radiation passing through the transmission fluid sample.

Figure 6:
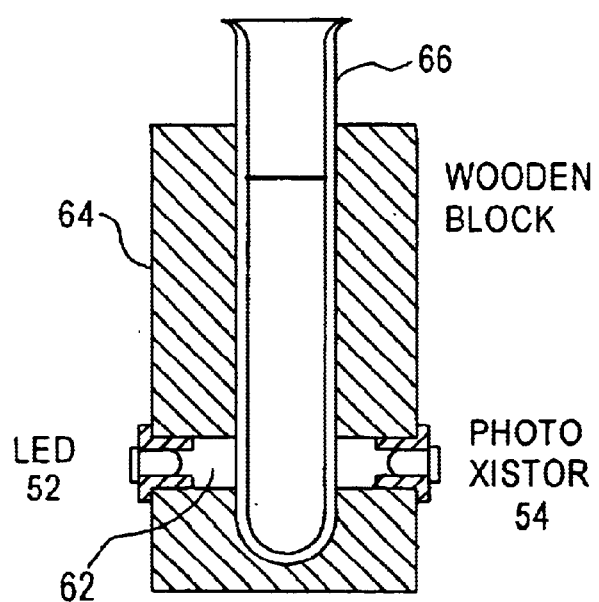
FIG. 6 illustrates an arrangement for inserting a fluid sample container of the present invention.

As illustrated in FIG. 6, the infrared LED 52 and the photo transistor 54 may be mounted opposite one another at either end of a hole 62 drilled through a block 64 of solid material such as wood. For example, the LED 52 and the phototransistor 54 may be arranged at a distance of 1.5 inches.

A transmission fluid sample may be held in a sample container 66 made of clear plastic or cellophane to minimize the radiation intensity required to penetrate the fluid sample under test. The container 66 receiving a transmission fluid sample from a dipstick may be inserted into a narrow slot drilled in the block 64 perpendicularly with respect to the hole 62. The narrow slot prevents outside light from influencing test results. For example, the diameter of the slot for inserting the fluid sample container 66 may be about 0.5 inches. The sample container 66 is disposable to prevent the tester 10 from being contaminated by the previously tested fluid samples.

Thus, the present invention provides an automatic transmission fluid tester for determining the remaining service life of automatic transmission fluid. The tester includes a radiation source for emitting radiation in the direction of a transmission fluid sample under test, and a radiation receiver for detecting radiation passed through the sample. Based on the output of the radiation receiver, the tester measures the opacity of the sample. The remaining service life of the automatic transmission fluid is determined as a function of the measured opacity.

In this disclosure, there is shown and described only one embodiment of the invention, but it is to be understood that the invention is capable of changes and modifications within the scope of the inventive concept as expressed herein. For example, the present invention may be implemented using any radiation source emitting radiation capable of passing the sample under test. Also, one skilled in the art would realize that the tester of the present invention may be implemented in a number of different ways. The tester may be implemented based on specifically engineered chips having logic circuits and other components for performing the functions described above. Alternatively, the tester may be implemented using a general-purpose digital signal processor and appropriate programming.

What is claimed is:

1. A system for testing automatic transmission fluid (ATF), comprising:
   a radiation source for emitting radiation in a direction of ATF under test,
   a radiation receiver responsive to the radiation for producing an output signal representing intensity of the radiation passed through the ATF, and
   an output circuit responsive to the output signal for determining condition of the ATF,
   the ATF under test being contained in a disposable container.

2. The system of claim 1, wherein the output circuit is configured to measure the opacity of the ATF.

3. The system of claim 1, wherein the output circuit is configured to compare the output signal with multiple calibration levels to provide a multiple level indication of the remaining service life of the ATF.

4. The system of claim 3, wherein each of the calibration levels corresponds to the output signal of the radiation receiver produced in response to the radiation passed through the ATF having known length of life.

5. The system of claim 4, wherein each of the calibration levels is maintained at the same level for a tested ATF of any type.

6. The system of claim 5, wherein the radiation source comprises a source of infrared radiation.

7. The system of claim 4, wherein the calibration levels are set for a particular type of a tested ATF.

8. The system of claim 7, wherein the radiation source comprises a source of red light.

9. The system of claim 1 further comprising a slot arranged between the radiation source and radiation receiver for receiving the disposable container.

10. The system of claim 1 further comprising a radiation controller for controlling radiation emitted by the radiation source.

11. The system of claim 10, wherein the radiation controller controls the radiation source to make the intensity of the emitted radiation sufficient to traverse the ATF under test.

12. The system of claim 11, wherein the radiation controller controls the radiation source so as to emit a predetermined sequence of radiation signals with progressively increasing intensity.

13. The system of claim 10, wherein the radiation controller controls the radiation source to emit pulse radiation signals.

14. The system of claim 13, wherein the output circuit is configured to compare duty cycle values of pulse signals at the output of the radiation receiver with calibration duty cycle values to determine the condition of the ATF under test.

15. A method of determining the remaining service life of ATF, comprising the steps of:

emitting radiation in a direction of ATF under test contained in a disposable container, measuring the opacity of the ATF based on the radiation passed through the ATF, and determining the remaining service life of the ATF as a function of the measured opacity.

16. The method of claim 13 further comprising the step of comparing a signal indicative of the opacity with multiple calibration levels to determine the remaining service life of the ATF under test.

17. The method of claim 16 wherein each of the multiple calibration levels is set in response to the radiation passed through the ATF having known length of life.

18. The method of claim 17, wherein the ATF under test is irradiated with infrared radiation to provide consistent indication of the remaining service life for ATF of various types.

19. The method of claim 18, wherein the ATF under test is irradiated with red light to increase the accuracy of determining the remaining service life of ATF of a particular type as a function of the measured opacity.

* * * * *